(12) United States Patent
Liu et al.

(10) Patent No.: US 11,642,477 B1
(45) Date of Patent: May 9, 2023

(54) MEASUREMENT DEVICE AND METHOD FOR MONITORING CONDITION OF PATIENT

(71) Applicant: TELESAIR, INC., Irvine, CA (US)

(72) Inventors: Yong Liu, Orange, CA (US); Qing Wang, Palo Alto, CA (US)

(73) Assignee: Telesair, Inc., Irvine, CA (US)

( * ) Notice: Subject to any disclaimer, the term of this patent is extended or adjusted under 35 U.S.C. 154(b) by 0 days.

(21) Appl. No.: 17/746,251

(22) Filed: May 17, 2022

(51) Int. Cl.
*A61M 16/00* (2006.01)
(52) U.S. Cl.
CPC ...... *A61M 16/0003* (2014.02); *A61M 16/024* (2017.08); *A61M 2016/003* (2013.01); *A61M 2016/0027* (2013.01); *A61M 2205/70* (2013.01); *A61M 2230/42* (2013.01)
(58) Field of Classification Search
CPC .... A61M 16/0003; A61M 16/024–026; A61M 2016/0027; A61M 2016/003; A61M 2205/70; A61M 2230/42
USPC .................................................... 128/204.23
See application file for complete search history.

(56) References Cited

U.S. PATENT DOCUMENTS

| 2012/0041279 A1* | 2/2012 | Freeman | A61B 5/0535 600/534 |
| 2013/0133651 A1* | 5/2013 | Barker | A61M 16/0066 128/203.14 |
| 2016/0030691 A1* | 2/2016 | Berry Ann | A61M 16/024 128/204.23 |

FOREIGN PATENT DOCUMENTS

WO    WO-2012095813 A1 *  7/2012  ........... A61B 5/0205

* cited by examiner

*Primary Examiner* — Elliot S Ruddie
(74) *Attorney, Agent, or Firm* — Maier & Maier, PLLC

(57) ABSTRACT

A measurement device and a method for monitoring a condition of a patient. The measurement device includes: a gas-guide apparatus, connected between an medical gas provider and a patient and configured to deliver medical gas from the medical gas provider to the patient; and at least one sensing apparatus, placed on an outer surface of the gas-guide apparatus and configured to detect real-time measurement data of the medical gas passing through the gas-guide apparatus. In this way, the at least one sensing apparatus is placed on the outer surface of the gas-guide apparatus, since the measurement data is a relative value which indicates a change of internal environment of the gas-guide apparatus, this can also avoid a problem of contamination compared with setting a sensor inside a respiratory device, thus improving the security of the measurement.

14 Claims, 7 Drawing Sheets

MEASUREMENT DEVICE AND METHOD FOR MONITORING CONDITION OF PATIENT

TECHNICAL FIELD

The present application relates to the technical field of medical treatment, and in particular, to a measurement device, a method for monitoring a condition of a patient, and a non-transitory computer readable storage medium.

BACKGROUND

A measurement device plays a key role in operation of a respiratory device. The respiratory device can be employed for a patient who is unable to ensure enough ventilation by their own respiratory efforts, for example, a patient who suffers from a respiratory disease caused by the COVID-19 virus.

The respiratory device's function is to assist the patient with respiratory insufficiency. The respiratory device exchanges gas and energy (such as thermal energy) through an apparatus such as a breathing circuit, a facial mask or a nasal cannula.

This background information is provided to reveal information believed by the applicant to be of possible relevance to the present application. No admission is necessarily intended, nor should be construed, that any of the preceding information constitutes prior art against the present application.

SUMMARY

Embodiments of the present application provide a measurement device, a method for monitoring a condition of a patient, and a non-transitory computer readable storage medium.

The foregoing and other objects are achieved by the subject matter of the independent claims. Further implementation forms are apparent from the dependent claims, the description and the figures.

A first aspect of the present application provides a measurement device, including:

a gas-guide apparatus, connected between a medical gas provider and a patient and configured to deliver medical gas from the medical gas provider to the patient; and at least one sensing apparatus, placed on an outer surface of the gas-guide apparatus and configured to detect real-time measurement data of the medical gas passing through the gas-guide apparatus.

In a possible implementation, the real-time measurement data indicates a change in at least one of an airway pressure, a gas flow rate and a respiratory rate.

In a possible implementation, a side wall of the gas-guide apparatus where the sensing apparatus is located is thinner or softer with respect to other positions of the side wall.

In a possible implementation, the at least one sensing apparatus includes at least one tactile sensor, and the at least one tactile sensor is arranged at a position close to an accessory muscle of the patient; and the measurement data indicates a real-time motion amplitude of the accessory muscle.

In a possible implementation, the at least one sensing apparatus includes a plurality of tactile sensors, and the plurality of tactile sensors are distributed along the gas-guide apparatus in array.

In a possible implementation, the at least one sensing apparatus includes at least one first tactile sensor and at least one second tactile sensor;

the gas-guide apparatus includes a front-end tube, a middle tube and a back-end tube connected in sequence, the front-end tube is arranged close to the patient, and the back-end tube is arranged close to the medical gas provider; and the at least one first tactile sensor is placed on an outer surface of the front-end tube, and the at least one second tactile sensor is placed on an outer surface of the back-end tube.

In a possible implementation, the front-end tube is a non-heated respiratory tube and the back-end tube is a heated respiratory tube.

In a possible implementation, the at least one sensing apparatus is further configured to:

determine whether the measurement data is abnormal according to a preset threshold; and in response to determining that the measurement data is abnormal, trigger an alarm signal.

In a possible implementation, the sensing apparatus is communicatively connected to a control device and configured to send the measurement data to the control device for analysis of the measurement data.

In a possible implementation, the at least one sensing apparatus is further configured to perform a preliminary filtering operation on the measurement data before sending the measurement data to the control device.

A second aspect of the present application provides a method for monitoring a condition of a patient, the method is executed by a control device, and the method includes:

receiving real-time measurement data sent by at least one sensing apparatus, where real-time measurement data indicates a change in at least one of an airway pressure, a gas flow rate, and a respiratory rate of medical gas delivered to the patient;

determining whether the real-time measurement data is abnormal; and in response to determining that the real-time measurement data is abnormal, adjusting an amount of the medical gas according to the real-time measurement data.

In a possible implementation, the sensing apparatus includes a plurality of tactile sensors distributed in an array;

the receiving the real-time measurement data sent by the at least one sensing apparatus includes:

receiving real-time measurement data detected by the plurality of tactile sensors respectively; and performing a calibration based on the received real-time measurement data to obtain calibrated measurement data;

the adjusting the amount of the medical gas according to the real-time measurement data includes:

adjusting the amount of the medical gas according to the calibrated measurement data.

In a possible implementation, the method further includes:

triggering an image capturing apparatus to capture a real-time image of the patient; and receiving the real-time image of the patient from the image capturing apparatus;

the adjusting the amount of the medical gas according to the real-time measurement data includes:

adjusting the amount of the medical gas according to the real-time measurement data and the real-time image of the patient.

In a possible implementation, where after the receiving the real-time image of the patient from the image capturing apparatus, the method further includes:

comparing the real-time image with a preset reference image to determine whether the real-time image is abnormal; and in response to determining that the real-time image is abnormal, sending alarm information to a client.

In a possible implementation, after the receiving the real-time measurement data sent by the at least one sensing apparatus, the method further includes:

analyzing the detected real-time measurement data to obtain a respiratory parameter;

generating data corresponding to a visual chart according to the respiratory parameter; and sending the data corresponding to the visual chart to a display apparatus.

In a possible implementation, where the determining whether the real-time measurement data is abnormal includes:

determining that the real-time measurement data is abnormal when the respiratory parameter is greater than a corresponding preset threshold; and the method further includes:

sending alarm information to a client.

A third aspect of the present application provides a non-transitory computer readable storage medium, where the computer readable storage medium is configured to store a computer program, and the computer program causes a computer to:

receive real-time measurement data sent by at least one sensing apparatus, where the real-time measurement data indicates a change in at least one of an airway pressure, a gas flow rate, and a respiratory rate of medical gas delivered to the patient;

determine whether the real-time measurement data is abnormal; and in response to determining that the real-time measurement data is abnormal, adjust an amount of the medical gas according to the real-time measurement data.

The present application provides a measurement device and a method for monitoring a condition of a patient. The measurement device includes: a gas-guide apparatus, connected between an medical gas provider and a patient and configured to deliver medical gas from the medical gas provider to the patient; and at least one sensing apparatus, placed on an outer surface of the gas-guide apparatus and configured to detect real-time measurement data of the medical gas passing through the gas-guide apparatus. In this way, the at least one sensing apparatus is placed on the outer surface of the gas-guide apparatus, since the collected measurement data is a relative value which indicates a change of internal environment of the gas-guide apparatus, this can avoid a problem of contamination compared with the manner of setting a sensor inside a respiratory device, thus improving the security of the measurement.

BRIEF DESCRIPTION OF DRAWINGS

The accompanying drawings are used to provide a further understanding of the present application, constitute a part of the specification, and are used to explain the present application together with the following specific embodiments, but should not be construed as limiting the present application.

DETAILED DESCRIPTION OF THE EMBODIMENTS

Figure 1:
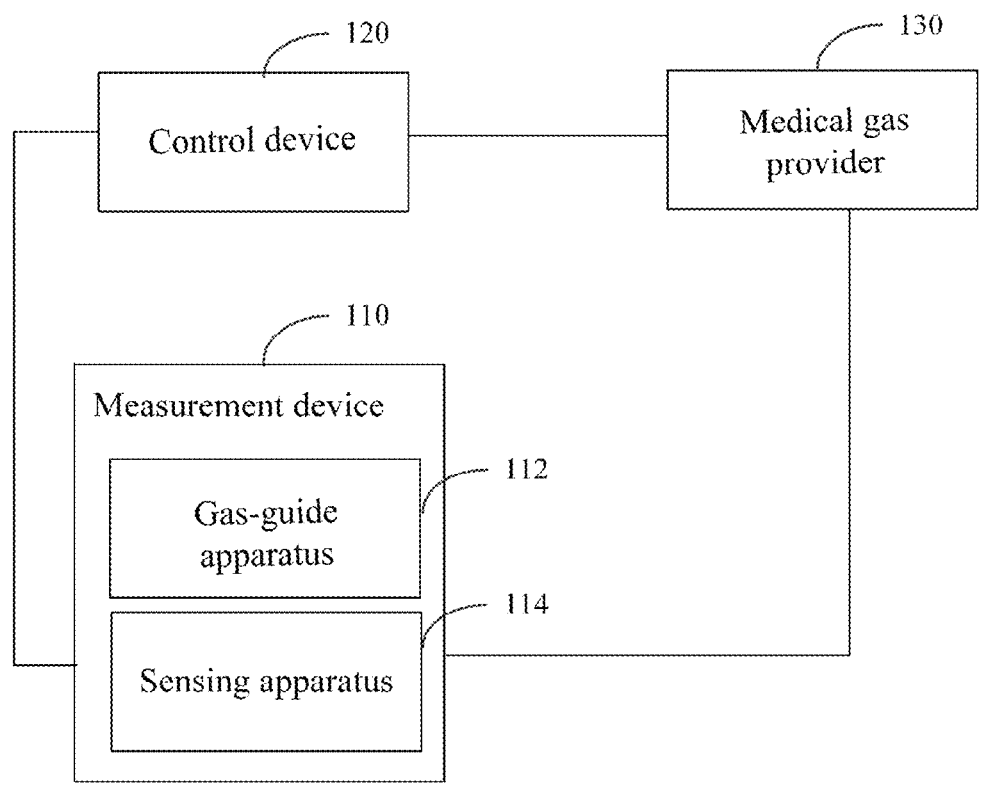
FIG. 1 illustrates a schematic diagram of a medical gas delivering system according to an embodiment of the present application.

In the following description, reference is made to the accompanying figures, which form part of the application, and which show, by way of illustration, specific aspects of embodiments of the present application or specific aspects in which embodiments of the present application may be used. It is understood that embodiments of the present application may be used in other aspects and include structural or logical changes not depicted in the figures. The following detailed description, therefore, is not to be taken in a limiting sense, and the scope of the present application is defined by the appended claims.

A respiratory device is widely used in the field of medical treatment. For example, when a patient suffers from a respiratory disease caused by the COVID-19 virus, the respiratory device can be employed to assist the patient with respiratory insufficiency. In general, a sensing apparatus is configured to detect measurement data and send the measurement data to a controller, then the controller provides an operation strategy for the respiratory device according to the measurement data.

In existing art, the measurement data monitored by the sensing apparatus is an absolute value, and the sensing apparatus may be as a pressure sensor and/or a flow sensor internal to the respiratory device for both invasive ventilation and non-invasive ventilation. For example, proximal sensors may be configured, i.e., the pressure sensor and/or the flow sensor may be placed in vicinity to a port of the patient. The proximal sensors placed in vicinity to the port of the patient are more sensitive to respiratory efforts of the patient since they are closer to airway of the patient. In this conventional way, these pressure and flow sensors close to the airway of the patient are also vulnerable to contamination from the airway of the patient. For example, since the sensors are placed in vicinity to the port of the patient, performance of the sensors may be affected by steam or gas passing through the airway, i.e., there exists a hazard by biocompatibility. In other words, there exists a problem of low security.

The present application provides a measurement device and a method for monitoring a condition of a patient and a respiratory device. The measurement device includes: a gas-guide apparatus, connected between an medical gas provider and a patient and configured to deliver medical gas from the medical gas provider to the patient; and at least one sensing apparatus, placed on an outer surface of the gas-guide apparatus and configured to detect real-time measurement data of the medical gas passing through the gas-guide apparatus. In this way, the at least one sensing apparatus is placed on the outer surface of the gas-guide apparatus, since the collected measurement data is a relative value which indicates a change of internal environment of the gas-guide apparatus, this can avoid a problem of contamination compared with the manner of setting a sensor inside a respiratory device, thus improving the security of the measurement.

In the following, the technical solutions of the present application will be described in detail with reference to the accompany drawings.

Illustratively, a medical gas delivering system 100 to which an embodiment of the present application is applied is shown in FIG. 1. The system 100 includes a measurement device 110, a control device 120 and a medical gas provider 130, where the measurement device 110 includes a gas-guide apparatus 112 and a sensing apparatus 114. The sensing apparatus 114 is configured to detect real-time measurement data of the medical gas passing through the gas-guide apparatus 112, the measurement device 110 is connected to the control device 120 and the medical gas provider 130 respectively, and the control device 120 is connected to the medical gas provider 130. The control device 120 regulates ventilation passing through the gas-guide apparatus 112 according to the real-time measurement data from the measurement device 110 by means of controlling the medical gas provider 130.

It should be noted that, the medical gas provider 130 may provide oxygen, compressed air, nitrogen, nitrous oxide, carbon dioxide and other gases according to actual needs. For example, the medical gas provider 130 may be an oxygen provider, and the control device 120 may be integrated in a respiratory device, or may be independent from the respiratory device. For example, the control device 120 and the oxygen provider are both integrated into a respiratory device, so that the respiratory device adjusts and provides oxygen-containing gas to a patient based on the real-time measurement data from the measurement device 110.

FIG. 1 illustratively shows the gas-guide apparatus 112, the sensing apparatus 114, the control device 120 and the medical gas provider 130, but the present application is not limited to such arrangement. The system 100 may include other devices, such as a regulating mechanism, a display assembly, etc.

An embodiment of the present application provides a measurement device 200, including:

a gas-guide apparatus 210, connected between an medical gas provider and a patient and configured to deliver medical gas from the medical gas provider to the patient; and at least one sensing apparatus 220, placed on an outer surface of the gas-guide apparatus 210 and configured to detect real-time measurement data of the medical gas passing through the gas-guide apparatus 210.

The medical gas provider delivers medical gas to a patient through the gas-guide apparatus, where the gas-guide apparatus 210 may be a flexible tube. The at least one sensing apparatus 220 is placed on the outer surface of the gas-guide apparatus 210, where the sensing apparatus may be a sensor which is sensitive to a change of the gas-guide apparatus 210 and can detect a specific change. For example, the sensing apparatus may include a pressure sensor, a flow sensor, a sound sensor, a motion sensor, a tactile sensor, etc.

The above measurement device provides patient monitoring for non-invasive respiratory support. In addition, the at least one sensing apparatus is placed on the outer surface of the gas-guide apparatus, since the collected measurement data is a relative value which indicates a change of the internal environment of the gas-guide apparatus, this can avoid a problem of contamination compared with the manner of setting a sensor inside a respiratory device, thereby improving the security of the measurement.

In a possible implementation, the real-time measurement data indicates a change in at least one of an airway pressure, a gas flow rate and a respiratory rate. The respiratory rate is used for describing the number of breaths per minute. The gas flow rate is a capacity parameter, and may be detected in a tube from an air inlet to an exhalation valve. The airway pressure is a mechanical ventilation parameter, and should be maintained within a normal range, thus ensuring normal ventilation of the patient. These parameters may indicate respiratory status of the patient, and are critical for adjusting an amount of medical gas.

In a possible implementation, a side wall of the gas-guide apparatus where the sensing apparatus is located is thinner or softer with respect to other positions of the side wall. On the one hand, this design makes it easier to install the sensing apparatus; on the other hand, in this way, accuracy of the measurement data may be improved.

In a possible implementation, the at least one sensing apparatus includes at least one tactile sensor, and the at least one tactile sensor is arranged at a position close to an accessory muscle of the patient; and the measurement data indicates a real-time motion amplitude of the accessory muscle.

The tactile sensor is made by flexible materials. The tactile sensor is a touch sensor which can provide information about an object in contact with it, and has an advantage of light weight, thus it is appropriate for the tactile sensor to be arranged on the outer surface of the gas-guide apparatus. The information may be the measurement data. The position close to the accessory muscle of the patient may be somewhere around the neck/the chest/the spine of the patient. The position may be convenient for the patient. When the position includes a position around the neck, the information may include a respiratory rate, which can be used for data calibration.

The tactile sensor may be printable, and can be printed on the respiratory device, wherever on the outer surface of nasal cannula, a tube, a connector, a strap or any other part of the device that directly or indirectly interfaces with the patient. The tactile sensor monitors a condition of the patient non-invasively.

In a possible implementation, the at least one sensing apparatus includes a plurality of tactile sensors, and the plurality of tactile sensors are distributed along the gas-guide apparatus in array. The measurement data acquired by each of the tactile sensors distributed in array may be measurement data from the same position, and can be used for a calibration, thus improving accuracy of the calibrated measurement data.

Figure 2:
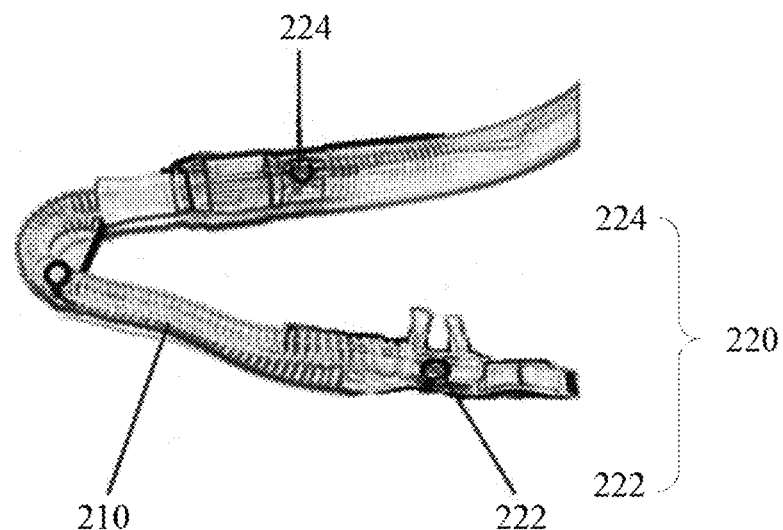
FIG. 2 illustrates a structural diagram of a measurement device according to an embodiment of the present application.

In a possible implementation, as shown in FIG. 2, the at least one sensing apparatus 220 includes at least one first tactile sensor 222 and at least one second tactile sensor 224;

the gas-guide apparatus 210 includes a front-end tube, a middle tube and a back-end tube connected in sequence, the front-end tube is arranged close to the patient, and the back-end tube is arranged close to the medical gas provider; and the at least one first tactile sensor 222 is placed on an outer surface of the front-end tube, and the at least one second tactile sensor 224 is placed on an outer surface of the back-end tube.

The first tactile sensor and the second tactile sensor are placed at different positions, the measurement data detected from different positions can be used for the calibration, thus improving accuracy of the calibrated measurement data. In a possible implementation, the front-end tube is a non-heated respiratory tube and the back-end tube is a heated respiratory tube. If moist air passes through the tube with a low temperature, condensation occurs; thus, the tube may produce noise, and condensed water will flow along the tube, which affects the use of the respiratory device. The heated respiratory tube is arranged close to the medical gas provider, when the moist air passes through the heated respiratory tube, since a temperature in the air is about the same as that of the heated respiratory tube, there exists no condensate. In this way, a problem of condensation is solved.

In a possible implementation, the at least one sensing apparatus is further configured to:

determine whether the measurement data is abnormal according to a preset threshold; and in response to determining that the measurement data is abnormal, trigger an alarm signal.

Taking the airway pressure as an example, when a change of the airway pressure exceeds a preset threshold, for example, 10%, it is considered that current airway pressure is abnormal, and the sensing apparatus triggers the alarm signal. The preset threshold can be set by a user according to actual needs. The user may be a physician, a caregiver, etc.

In a possible implementation, the sensing apparatus is communicatively connected to a control device and configured to send the measurement data to the control device for analysis of the measurement data. The sensing apparatus may be connected to the control device via a wired connection or in a wireless manner. The control device may be integrated in the respiratory device, or may be independent from the respiratory device.

In a possible implementation, the at least one sensing apparatus is further configured to perform a preliminary filtering operation on the measurement data before sending the measurement data to the control device. Interference signals may be removed through the preliminary filtering operation, for example, the measurement data during a non-monitoring period may not be sent to the control device. In this way, the subsequent processing of the control device can be more efficient. The subsequent processing may include deciding a ventilation mode and specific parameters provided to the patient.

Figure 3:
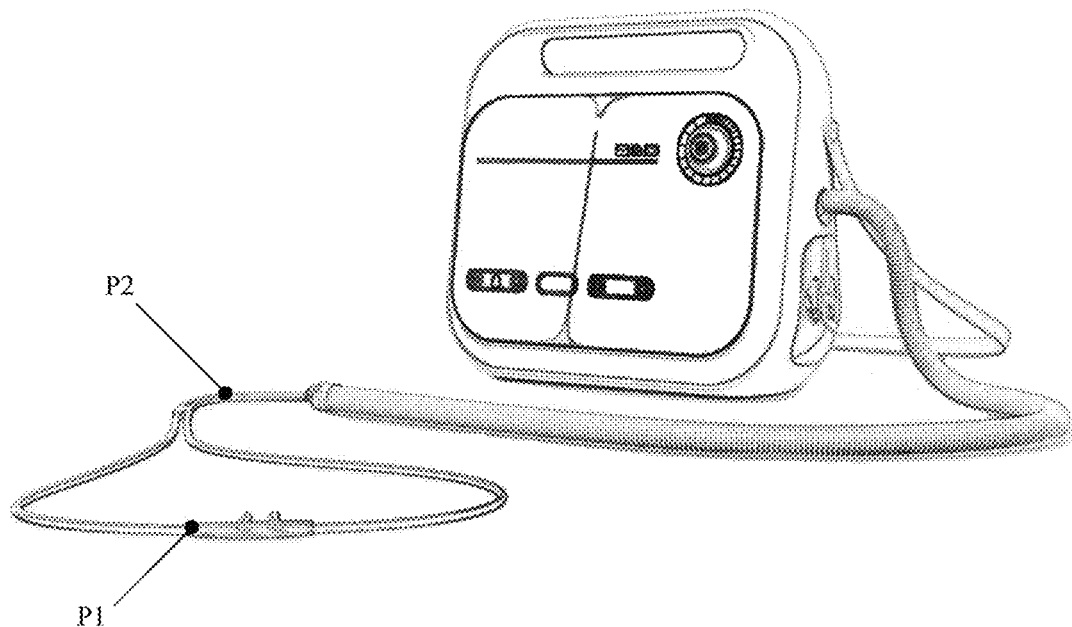
FIG. 3 illustrates an exemplary scenario of the measurement device according to an embodiment of the present application.
Figure 4:
FIG. 4 illustrates an exemplary scenario of the measurement device according to another embodiment of the present application.

An exemplary scenario of the measurement device may be shown as FIG. 3 and FIG. 4, in the figures, positions of the sensors are only illustrative. The measurement device may be connected to a body of the respiratory device. For example, as shown in FIG. 3 and FIGS. 4, P1 and P3 represent positions at which a pressure sensor for detecting respiratory efforts may be located, and P2 and P4 represent positions at which a pressure sensor for detecting a motion amplitude of an accessary muscle may be located, for example, when using this device, P2 and P4 would be locations around the neck/the chest/the spine of the patient.

Figure 5:
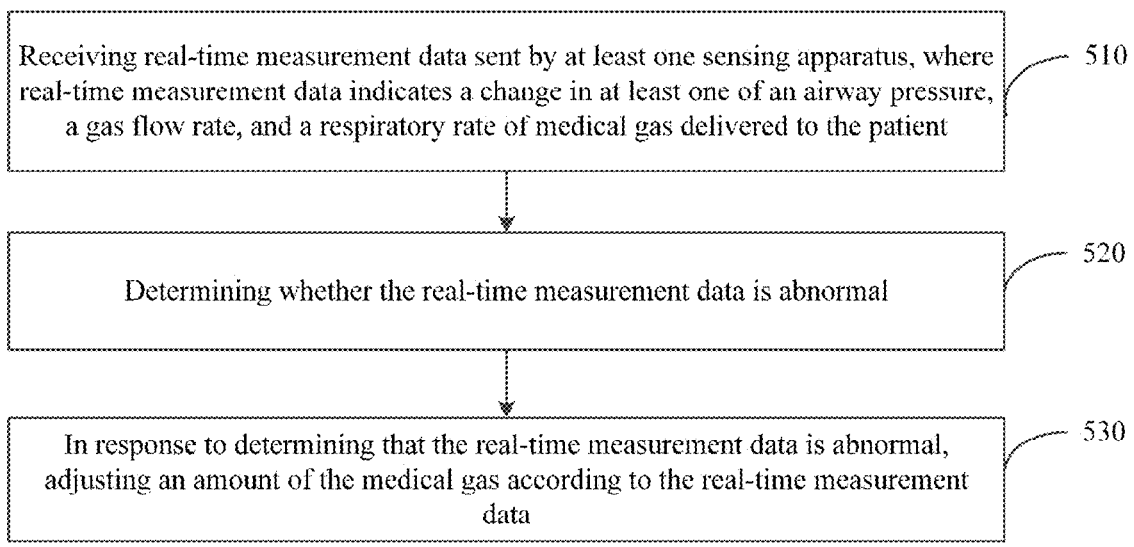
FIG. 5 illustrates a schematic flowchart of a method for monitoring a condition of a patient according to an embodiment of the present application.

An embodiment of the present application provides a method for monitoring a condition of a patient, the method is executed by a control device. As shown in FIG. 5, the method includes the following steps.

Step 510: receiving real-time measurement data sent by at least one sensing apparatus, where real-time measurement data indicates a change in at least one of an airway pressure, a gas flow rate, and a respiratory rate of medical gas delivered to the patient.

The gas flow rate is a capacity parameter, and may be detected in a tube from an air inlet to an exhalation valve. The airway pressure is a mechanical ventilation parameter. The gas flow rate and the airway pressure should be maintained within a normal range, thus ensuring normal ventilation of the patient. These parameters may indicate respiratory status of the patient and are critical for adjusting an amount of medical gas. The at least one sensing apparatus may be placed on an outer surface of the gas-guide apparatus and configured to detect the real-time measurement data of the medical gas passing through the gas-guide apparatus.

Step 520: determining whether the real-time measurement data is abnormal.

The real-time measurement data may be compared with a preset range to determine whether real-time measurement data is abnormal, where the preset range may be acquired based on data from experiments. For example, when the real-time measurement data is within the preset range, it is determined that the real-time measurement data is normal; and when the real-time measurement data is beyond the preset range, it is determined that the real-time measurement data is abnormal. The implementation manner of determining is not limited herein.

Step 530: in response to determining that the real-time measurement data is abnormal, adjusting an amount of the medical gas according to the real-time measurement data.

For example, when it is determined that a change of the current respiratory rate is abnormal, specifically, it indicates the current respiratory rate is higher than the upper limit of a normal range, then the amount of the medical gas may be increased.

As stated above, since the measurement data is a relative value which indicates a change of internal environment of the gas-guide apparatus, this can avoid a problem of contamination compared with the manner of setting a sensor inside a respiratory device.

Figure 6:
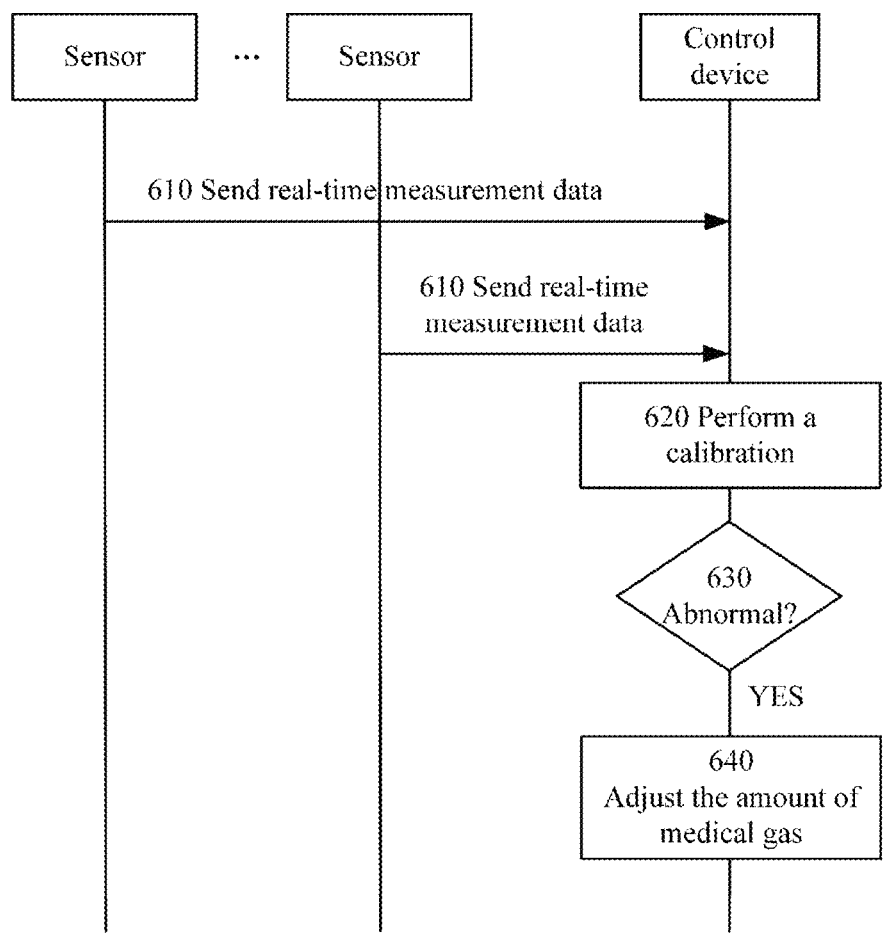
FIG. 6 illustrates a schematic flowchart of a method for monitoring a condition of a patient according to another embodiment of the present application.

In a possible implementation, the sensing apparatus includes a plurality of tactile sensors distributed in an array, as shown in FIG. 6, the method includes:

step 610: a plurality of tactile sensors send real-time measurement data to a control device respectively, and the control device receives the real-time measurement data sent by the plurality of tactile sensors;

step 620: the control device performs a calibration based on the received real-time measurement data to obtain calibrated measurement data;

step 630: the control device determines whether the real-time measurement data is abnormal; and step 640: in response to determining that the real-time measurement data is abnormal, the control device adjusts the amount of the medical gas according to the calibrated measurement data.

The implementations of steps 610, 630 and 640 are similar to steps 510, 520 and 530 respectively, which are not described herein.

Regarding step 620, the measurement data acquired by each of the tactile sensors distributed in array may be measurement data from the same position, and can be used for a calibration, thus improving accuracy of final measurement data. For example, there are three tactile sensors distributed in an array to monitor data of a position P1, the detected measurement data are referred to as D1, D2 and D3 respectively. Then, similarities are computed, that is, a first similarity S1 between D1 and D2, a second similarity S2 between D1 and D3, and a third similarity S3 between D2 and D3. If the similarity is less than a preset value, it is considered that corresponding measurement data may be abnormal. For example, if S1 and S2 are lower than the pre-set value, and S3 is higher than the pre-set value, it is considered that the measurement data D1 may be abnormal. Then the measurement data D1 may be deleted, and an average operation is performed on the measurement data D2 and D3 to obtain the calibrated measurement data. The implementation manner of computing similarities is not limited herein.

The measurement data is calibrated based on the real-time measurement data detected by the plurality of tactile sensors, in this way, in a case where a failure of one sensor occurs, accuracy of the measurement data can still be ensured.

Figure 7:
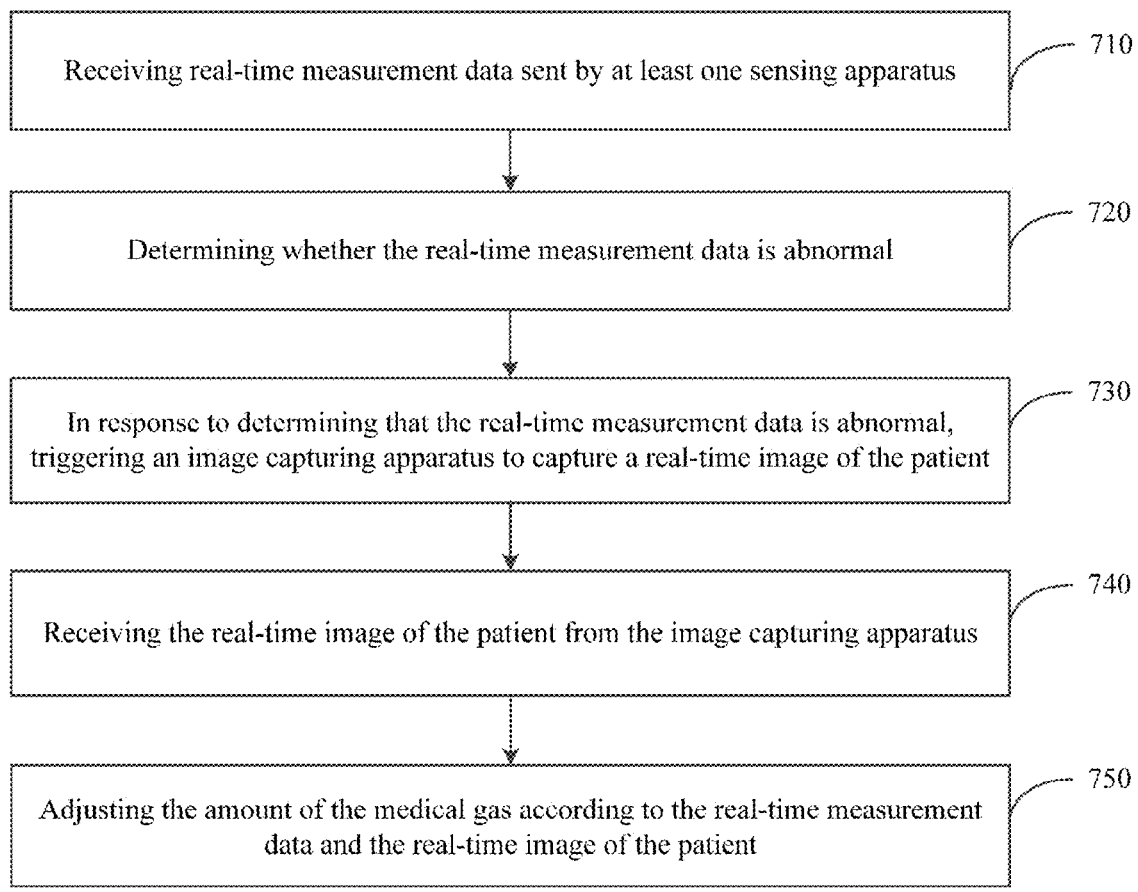
FIG. 7 illustrates a schematic flowchart of a method for monitoring a condition of a patient according to yet other embodiment of the present application.

In a possible implementation, as shown in FIG. 7, where the method includes:

step 710: receiving real-time measurement data sent by at least one sensing apparatus;

step 720: determining whether the real-time measurement data is abnormal;

step 730: in response to determining that the real-time measurement data is abnormal, triggering an image capturing apparatus to capture a real-time image of the patient;

step 740: receiving the real-time image of the patient from the image capturing apparatus; and step 750: in response to determining that the real-time measurement data is abnormal, adjusting the amount of the medical gas according to the real-time measurement data and the real-time image of the patient.

The implementations of steps 710 and 720 are similar to steps 510 and 520 respectively, which are not described herein.

Regarding steps 730 to 750, the accessory muscle may be an accessory muscle located at somewhere around the neck/the chest/the spine of the patient. The image capturing apparatus may be a camera. Taking the respiratory rate as an example, different respiratory rates may correspond to different motion amplitudes of the accessory muscle. The real-time measurement data may indicate a respiratory rate detected by a sensor placed on the outer surface of the gas-guide apparatus. When it is determined that the indicated respiratory rate is abnormal, the image capturing apparatus is triggered to capture the real-time image of the patient. The image capturing apparatus may be connected to the control device via a wired connection or in a wireless manner, for example, the control device may transmit a signal to the image capturing apparatus, and the signal is used for triggering the image capturing apparatus to capture the real-time image of the patient. Thus, the real-time motion amplitude of the accessory muscle can be obtained through analysis of the images of the accessory muscle. Extensive information related to the accessory muscle can be captured based on the real-time motion amplitude of the accessory muscle.

The camera is combined with the sensing apparatus to monitor the condition of the patient, which is traditionally done by a tour of inspection of a physician or other caregivers. Through combining information provided by the camera and the sensing apparatus, a condition of the patient can be evaluated and decided timely and effectively. Thus, an optimal treatment decision can be achieved by the physician. Moreover, the above method is a non-invasive monitoring method, and can monitor the condition of the patient without any additional interfering object to the patient besides the respiratory device per se.

In a possible implementation, after the receiving the real-time image of the patient from the image capturing apparatus, the method further includes:

comparing the real-time image with a preset reference image to determine whether the real-time image is abnormal; and in response to determining that the real-time image is abnormal, sending alarm information to a client.

The client may be a client (an operating end such as a smart phone) of medical staff, such as a physician and a caregiver. The alarm information may include an alarm signal, and when the physician or the caregiver receives the alarm signal, he or she can reach a place where the patient is and observe the condition of the patient immediately. This can help the medical staff monitoring real-time condition of the patient effectively. The alarm information may further include the abnormal image, thus the physician or the caregiver can determine urgency of multiple events to make a right decision. Moreover, abnormal images can be stored for other requirements. The preset reference image may be an image captured in advance when the patient is in a normal condition.

In a possible implementation, after receiving the real-time measurement data sent by the at least one sensing apparatus, the method further includes:

analyzing the detected real-time measurement data to obtain a respiratory parameter;

generating data corresponding to a visual chart according to the respiratory parameter; and sending the data corresponding to the visual chart to a display apparatus.

The real-time measurement data is output data of the sensing apparatus, for example, it may be in a form of electrical signals, hence, it is necessary to perform analysis on output data of the sensing apparatus to obtain a simple visual representation. The respiratory parameter may be an airway pressure, a gas flow rate and a respiratory rate, etc. In addition, a change of the respiratory parameter with time may be shown in a form of a chart. A user can observe the change through the chart, thus improving user experience.

In a possible implementation, where the determining whether the real-time measurement data is abnormal includes:

determining that the real-time measurement data is abnormal when the respiratory parameter is greater than a corresponding preset threshold; and the method further includes:

sending alarm information to a client.

Taking the airway pressure as an example, when a change of the airway pressure exceeds a preset threshold, for example, 10%, it is considered that current airway pressure is abnormal, and the control device sends the information to the client. The preset threshold can be set by a user through the client according to actual needs. The client may be a client of medical staff, such as a physician and a caregiver. This can help the medical staff monitoring real-time condition of the patient effectively.

Figure 8:
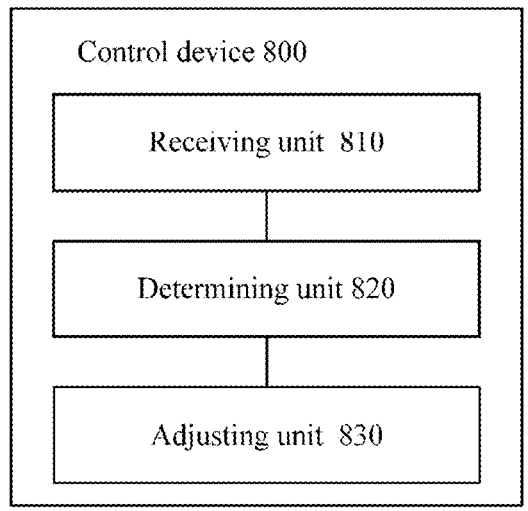
FIG. 8 illustrates a block diagram of a control device according to an embodiment of the present application.

FIG. 8 illustrates a block diagram of a control device according to an embodiment of the present application. As shown in FIG. 8, a control device 800 includes:

a receiving unit 810, configured to receive real-time measurement data sent by at least one sensing apparatus, where the real-time measurement data indicates a change in at least one of an airway pressure, a gas flow rate, and a respiratory rate of medical gas delivered to the patient;

a determining unit 820, configured to determine whether the real-time measurement data is abnormal; and an adjusting unit 830, configured to in response to determining that the real-time measurement data is abnormal, adjust an amount of the medical gas according to the real-time measurement data.

In a possible implementation, the sensing apparatus includes a plurality of tactile sensors distributed in an array, and the receiving unit 810 is configured to receive real-time measurement data detected by the plurality of tactile sensors respectively; the control device 800 further includes: a calibrating unit, configured to perform a calibration based on the received real-time measurement data to obtain calibrated measurement data; and the adjusting unit 830 is configured to adjust the amount of the medical gas according to the calibrated measurement data.

In a possible implementation, the control device 800 further includes: a processing unit, configured to in response to determining that the real-time measurement data is abnormal, trigger an image capturing apparatus to capture a real-time image of the patient; the receiving unit 810 is further configured to receive the real-time image of the patient from the image capturing apparatus; and the adjusting unit 830 is configured to adjust the amount of the medical gas according to the real-time measurement data and the real-time image of the patient.

In a possible implementation, the processing unit is further configured to compare the real-time image with a preset reference image to determine whether the real-time image is abnormal; and in response to determining that the real-time image is abnormal, send alarm information to a client.

In a possible implementation, the control device further includes an analyzing unit, configured to analyze the detected real-time measurement data to obtain a respiratory parameter; a generating unit, configured to generate data corresponding to a visual chart according to the respiratory parameter; and a sending unit, configured to send the data corresponding to the visual chart to a display apparatus.

In a possible implementation, the determining unit 820 is further configured to determine that the real-time measurement data is abnormal when the respiratory parameter is greater than a corresponding preset threshold; and the sending unit is further configured to send alarm information to a client.

Figure 9:
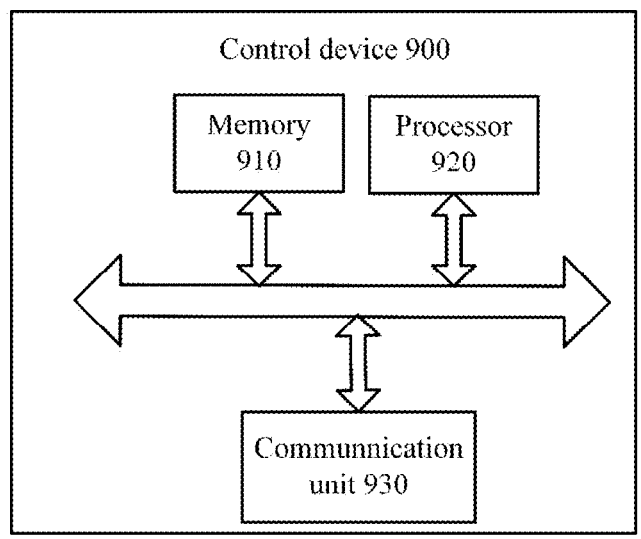
FIG. 9 illustrates a schematic structural diagram of a control device according to an embodiment of the present application.

As shown in FIG. 9, a control device 900 may include a memory 910 and a processor 920, where a computer program is stored in the memory 910, and configured to be executed by the processor 920 to implement the steps described in the above embodiments. In addition, the control device 900 may further include a communication unit 930 for communicating with a sensing apparatus and/or a client. The computer program (also known as programs, software, software applications, or codes) include machine instructions for a programmable processor, and may be implemented using high-level procedural and subtended programming languages, or assembly/machine languages.

An embodiment of the present application provides a non-transitory computer readable storage medium, where the computer readable storage medium is configured to store a computer program, and the computer program causes a computer to execute steps of:

receiving real-time measurement data sent by at least one sensing apparatus, where the real-time measurement data indicates a change in at least one of an airway pressure, a gas flow rate, and a respiratory rate of medical gas delivered to the patient;

determining whether the real-time measurement data is abnormal; and in response to determining that the real-time measurement data is abnormal, adjusting an amount of the medical gas according to the real-time measurement data.

In a possible implementation, where the sensing apparatus includes a plurality of tactile sensors distributed in an array;

the receiving the real-time measurement data sent by the at least one sensing apparatus includes:

receiving real-time measurement data detected by the plurality of tactile sensors respectively; and performing a calibration based on the received real-time measurement data to obtain calibrated measurement data;

the adjusting the amount of the medical gas according to the real-time measurement data includes:

adjusting the amount of the medical gas according to the calibrated measurement data.

In a possible implementation, further including:

in response to determining that the real-time measurement data is abnormal, triggering an image capturing apparatus to capture a real-time image of the patient; and receiving the real-time image of the patient from the image capturing apparatus;

the adjusting the amount of the medical gas according to the real-time measurement data includes:

adjusting the amount of the medical gas according to the real-time measurement data and the real-time image of the patient.

In a possible implementation, where the performing, based on the current motion amplitude of the accessory muscle, the calibration on the detected real-time measurement data to obtain the calibrated measurement data includes:

comparing the real-time image with a preset reference image to determine whether the real-time image is abnormal; and in response to determining that the real-time image is abnormal, sending alarm information to a client.

In a possible implementation, where after the receiving the real-time measurement data sent by the at least one sensing apparatus, the method further includes:

analyzing the detected real-time measurement data to obtain a respiratory parameter;

generating data corresponding to a visual chart according to the respiratory parameter; and sending the data corresponding to the visual chart to a display apparatus.

In a possible implementation, where the determining whether the real-time measurement data is abnormal includes:

determining that the real-time measurement data is abnormal when the respiratory parameter is greater than a corresponding preset threshold; and the method further includes:

sending alarm information to a client.

It should be understood by a person skilled in the art that, the relevant description of the above steps in the embodiments of the present application may be understood with reference to the relevant description of the method for monitoring a condition of a patient in the embodiments of the present application.

The term such as "and/or" in the embodiments of the present application is merely used to describe an association between associated objects, which indicates that there may be three relationships, for example, A and/or B may indicate presence of A only, of both A and B, and of B only.

The term "a" or "an" is not intended to specify one or a single element, instead, it may be used to represent a plurality of elements where appropriate.

In the embodiments of the present application, expressions such as "exemplary" or "for example" are used to indicate illustration of an example or an instance. In the embodiments of the present application, any embodiment or design scheme described as "exemplary" or "for example" should not be interpreted as preferred or advantageous over other embodiments or design schemes. In particular, the use of "exemplary" or "for example" is aimed at presenting related concepts in a specific manner.

It should be appreciated that, steps may be reordered, added, or deleted according to the various processes described above. For example, the steps described in the present application may be executed in parallel, sequentially, or in different orders, which are not limited herein as long as the desired results of the technical solutions disclosed in the present application can be achieved.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this application. A computer program product may include a computer-readable medium.

Finally, it should be noted that the foregoing embodiments are merely intended for describing the technical solutions of the present invention other than limiting the present invention. Although the present invention is described in detail with reference to the foregoing embodiments, a person of ordinary skill in the art should understand that he may still make modifications to the technical solutions described in the foregoing embodiments, or make equivalent replacements to some technical features thereof, without departing from the spirit and scope of the technical solutions of the embodiments of the present invention.

The invention claimed is:

1. A measurement device, comprising:
a gas-guide apparatus configured to connect between a medical gas provider and a patient side of the measurement device, and deliver medical gas from the medical gas provider to the patient; and
at least one sensing apparatus placed on an outer surface of the gas-guide apparatus and configured to detect real-time measurement data of the medical gas passing through the gas-guide apparatus; wherein the at least one sensing apparatus comprises:
at least one first tactile sensor and
at least one second tactile sensor; wherein the gas-guide apparatus comprises:
a front-end tube,
a middle tube, and
a back-end tube connected in sequence, the front-end tube is arranged close to the patient, and the back-end tube is arranged close to the medical gas provider; and the at least one first tactile sensor is placed on an outer surface of the front-end tube, and the at least one second tactile sensor is placed on an outer surface of the back-end tube.

2. The measurement device according to claim 1, wherein the real-time measurement data indicates a change in at least one of an airway pressure, a gas flow rate, and a respiratory rate.

3. The measurement device according to claim 1, wherein a side wall of the gas-guide apparatus where the sensing apparatus is located is thinner or softer with respect to other positions of the side wall.

4. The measurement device according to claim 1, wherein the front-end tube is a non-heated respiratory tube and the back-end tube is a heated respiratory tube.

5. The measurement device according to claim 1, wherein the at least one sensing apparatus is further configured to:
determine whether the measurement data is abnormal according to a preset threshold; and in response to determining that the measurement data is abnormal, trigger an alarm signal.

6. The measurement device according to claim 1, wherein the sensing apparatus is communicatively connected to a control device and configured to send the measurement data to the control device for analysis of the measurement data.

7. The measurement device according to claim 6, wherein the at least one sensing apparatus is further configured to perform a preliminary filtering operation on the measurement data before sending the measurement data to the control device.

8. The measurement device according to claim 1, wherein the gas-guide apparatus comprises a flexible tube.

9. A method for monitoring a condition of a patient, wherein the method is executed by a control device, and the method comprises:
receiving real-time measurement data from the measurement device according to claim 1, wherein the real-time measurement data indicates a change in at least one of an airway pressure, a gas flow rate, and a respiratory rate of medical gas delivered to the patient;
determining whether the real-time measurement data is abnormal; and
in response to determining that the real-time measurement data is abnormal, adjusting an amount of the medical gas according to the real-time measurement data.

10. A non-transitory computer readable storage medium, wherein the non-transitory computer readable storage medium is configured to store a computer program, and the computer program causes a computer to:
receive real-time measurement data from the measurement device according to claim 1, wherein the real-time measurement data indicates a change in at least one of an airway pressure, a gas flow rate, and a respiratory rate of medical gas delivered to the patient;
determine whether the real-time measurement data is abnormal; and
in response to determining that the real-time measurement data is abnormal, adjust an amount of the medical gas according to the real-time measurement data.

11. A method for monitoring a condition of a patient, wherein the method is executed by a control device, and the method comprises:

receiving real-time measurement data from a measurement device, wherein the real-time measurement data indicates a change in at least one of an airway pressure, a gas flow rate, and a respiratory rate of medical gas delivered to the patient; wherein the measurement device comprises a gas-guide apparatus and at least one sensing apparatus, the gas-guide apparatus is configured to connect between a medical gas provider and a patient side of the measurement device, and deliver medical gas from the medical gas provider to the patient; and the at least one sensing apparatus is placed on an outer surface of the gas-guide apparatus and configured to detect the real-time measurement data of the medical gas passing through the gas-guide apparatus;

determining whether the real-time measurement data is abnormal; and in response to determining that the real-time measurement data is abnormal, adjusting an amount of the medical gas according to the real-time measurement data; wherein the sensing apparatus comprises a plurality of tactile sensors distributed in an array; the receiving the real-time measurement data from the measurement device comprises:

receiving real-time measurement data detected by the plurality of tactile sensors respectively; and performing a calibration based on the received real-time measurement data to obtain calibrated measurement data; the adjusting the amount of the medical gas according to the real-time measurement data comprises:

adjusting the amount of the medical gas according to the calibrated measurement data.

12. A method for monitoring a condition of a patient, wherein the method is executed by a control device, and the method comprises:

receiving real-time measurement data from a measurement device, wherein the real-time measurement data indicates a change in at least one of an airway pressure, a gas flow rate, and a respiratory rate of medical gas delivered to the patient; wherein the measurement device comprises a gas-guide apparatus and at least one sensing apparatus, the gas-guide apparatus is configured to connect between a medical gas provider and a patient side of the measurement device, and deliver medical gas from the medical gas provider to the patient; and the at least one sensing apparatus is placed on an outer surface of the gas-guide apparatus and configured to detect the real-time measurement data of the medical gas passing through the gas-guide apparatus;

determining whether the real-time measurement data is abnormal; and in response to determining that the real-time measurement data is abnormal, adjusting an amount of the medical gas according to the real-time measurement data;

wherein the method further comprises:

triggering an image capturing apparatus to capture a real-time image of the patient; and receiving the real-time image of the patient from the image capturing apparatus;

the adjusting the amount of the medical gas according to the real-time measurement data comprises:

adjusting the amount of the medical gas according to the real-time measurement data and the real-time image of the patient.

13. The method according to claim 12, wherein after the receiving of the real-time image of the patient from the image capturing apparatus, the method further comprises:

comparing the real-time image with a preset reference image to determine whether the real-time image is abnormal; and in response to determining that the real-time image is abnormal, sending alarm information to a client.

14. The method according to claim 12, wherein the determining of whether the real-time measurement data is abnormal further comprises:

determining that the real-time measurement data is abnormal when the respiratory parameter is greater than a corresponding preset threshold; and the method further comprises:

sending alarm information to a client.

\* \* \* \* \*